United States Patent [19]

Johnston

[11] Patent Number: 4,906,095

[45] Date of Patent: Mar. 6, 1990

[54] APPARATUS AND METHOD FOR PERFORMING TWO-FREQUENCY INTERFEROMETRY

[75] Inventor: Roger G. Johnston, Los Alamos, N. Mex.

[73] Assignee: The United States of America as represented by the United States Department of Energy, Washington, D.C.

[21] Appl. No.: 147,468

[22] Filed: Jan. 25, 1988

[51] Int. Cl.[4] .............................................. G01B 9/02
[52] U.S. Cl. ..................................... 356/349; 356/361
[58] Field of Search ................. 356/357, 361, 362, 128

[56] References Cited

U.S. PATENT DOCUMENTS

| | | | |
|---|---|---|---|
| 4,229,105 | 10/1980 | Silverbage | 356/361 X |
| 4,447,153 | 5/1984 | Cremers et al. | 356/361 |
| 4,477,187 | 10/1984 | Pettit et al. | 356/349 X |
| 4,565,449 | 1/1986 | Grego | 356/349 X |

OTHER PUBLICATIONS

Koronkevich et al., "Interference Microscope with a Frequency Shift for the Investigation of the Refractive-Index Profiles of Glass Fibers", *Sov. J. Quant. Elec.*, vol. 9, No. 10, pp. 1332-1334, 10/79.
P. Hariharan, *Optical Interferometry*, Academic Press, New York (1985).
T. D. Harris, "High-Sensitivity Spectrophotometry," Analyt. Chem. 54(6), 741A-750A (1982).
David A. Cremers et al., "Thermooptic-Based Differential Measurements of Weak Solute Absorptions With an Interferometer," Appl. Opt. 21(9), 1654-1662 (1982).
L. Chen et al., "Photothermal Detection for Light-Scattering Material by Laser Interferometry," Appl. Phys. Lett. 50(19), 1340-1342 (1987).
Christopher C. Davis et al., "Phase Fluctuation Optical Heterodyne Spectroscopy of Gases," Appl. Opt. 20(14), 2539-2554 (1981).

*Primary Examiner*—Vincent P. McGraw
*Assistant Examiner*—Matthew W. Koren
*Attorney, Agent, or Firm*—Samuel M. Freund; Paul D. Gaetjens; William R. Moser

[57] ABSTRACT

The present apparatus includes a two-frequency, Zeeman-effect laser and matched, doubly refracting crystals in the construction of an accurate interferometer. Unlike other interferometric devices, the subject invention exhibits excellent phase stability owing to the use of single piece means for producing parallel interferometer arms, making the interferometer relatively insensitive to thermal and mechanical instabilities. Interferometers respond to differences in optical path length between their two arms. Unlike many interferometric techniques, which require the measurement of the location of interference fringes in a brightly illuminated background, the present invention permits the determination of the optical path length difference by measuring the phase of an electronic sine wave. The present apparatus is demonstrated as a differential thermooptic spectrometer for measuring differential optical absorption simply and accurately which is but one of many applications therefor. The relative intensities of the heating beams along each arm of the interferometer can be easily adjusted by observing a zero phase difference with identical samples when this condition is obtained.

25 Claims, 6 Drawing Sheets

APPARATUS AND METHOD FOR PERFORMING TWO-FREQUENCY INTERFEROMETRY

BACKGROUND OF THE INVENTION

The present invention relates generally to interferometry and, more particularly, to the use of a source of two-frequency electromagnetic radiation and polarization responsive beam splitting and recombining materials to distinctly define the two arms of a mechanically and thermally stable interferometer. One demonstrated application is the use of the such an interferometer for thermooptic spectroscopy. This present invention is the result of a contract between the U.S. Department of Energy and the University of California (Contract No. W-7405-ENG-36).

Interferometry is utilized for a wide variety of applications. Among the most interesting are the precise measurement of birefringence and refractive index, the measurement of phase differential light scattering, the measurement of motion, the measurement of length and thickness, and spectrophotometric determinations. See, e.g., *Optical Interferometry* by P. Hariharan, Academic Press, New York (1985), for a general reference on interferometric techniques and their applications. In all situations, complicated apparatus is employed. A summary of spectrophotometric techniques is presented in "High-Sensitivity Spectrophotometry" by T. D. Harris, Analyt. Chem. 54, 741A (1982). A more detailed account of thermooptic spectrophotometry is given in U.S. Pat. No. 4,447,153, "Apparatus And Method For Quantitative Measurement of Small Differences In Optical Absorptivity Between Two Samples Using Differential Interferometry and The Thermooptic Effect," issued to David A. Cremers and Richard A. Keller on May 8, 1984, and in "Thermooptic-Based Differential Measurements of Weak Solute Absorptions With An Interferometer" by David A. Cremers and Richard A. Keller, Appl. Opt. 21, 1654 (1982). The apparatus described therein is very complex. Another interferometric method for measuring photothermally induced refractive index variation is described in "Photothermal Detection For Light-Scattering Material By Laser Interferometry" by L. Chen and S. Y. Zhang, Appl. Phys. Lett. 50, 1340 (1987). In "Phase Fluctuation Optical Heterodyne Spectroscopy of Gases" by Christopher C. Davis and Samuel J. Petuchowski, Appl. Opt. 20, 2539 (1981), the authors describe a complicated method for studying molecular relaxation, thermal conduction, and extremely weak absorptions in the gas phase.

Accordingly, it is an object of the present invention to provide a simple, compact, vibrationally and thermally stable interferometer.

Another object of the present invention is to provide a simple, compact, vibrationally and thermally stable apparatus for measuring differential optical absorption.

Additional objects, advantages and novel features of the invention will be set forth in part in the description which follows, and in past will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the apparatus for measuring the optical phase difference resulting from a difference in index of refraction between a sample under investigation and a reference sample may include: a light source for providing a first wavelength of electromagnetic radiation and a second wavelength of electromagnetic radiation, the first radiation and the second radiation being substantially collinear, having substantially orthogonal polarization and an initial relative phase, and differing in wavelength by between $1 \times 10^{-13}$ nm and $7 \times 10^{-4}$ nm, radiation separation means responsive to polarization for spatially separating the first wavelength of radiation and the second of radiation into substantially parallel wavelengths of radiation, the first wavelength of radiation passing through the sample under investigation and the second wavelength of radiation passing through the reference sample, radiation combining means responsive to polarization for spatially reuniting the first wavelength of radiation and the second wavelength of radiation into substantially collinear wavelength of radiation after emergence thereof from their respective samples, polarization means for enabling the interference of the first wavelength of radiation and second wavelength of radiation, electromagnetic radiation detection means for generating an electrical interference signal in response thereto, and phase detection means for measuring the phase thereof relative to the initial relative phase of the first wavelength of radiation and the second wavelength of radiation.

In a further aspect of the present invention, in accordance with its objects and purposes, the method for measuring the optical phase difference resulting from a difference in index of refraction between a sample under investigation and a reference sample hereof may include generating a first wavelength of electromagnetic radiation and a second wavelength of electromagnetic radiation, the first radiation and the second radiation being substantially collinear, having substantially orthogonal polarization and an initial relative phase, and differing in wavelength by between $1 \times 10^{-13}$ nm and $7 \times 10^{-4}$ nm, spatially separating the first wavelength of radiation and the second wavelength of radiation by utilizing the difference in polarization thereof into substantially parallel wavelengths of radiation, directing the first wavelength of radiation into the sample under investigation, directing the second wavelength of radiation into the reference sample, spatially combining the first wavelength of radiation and the second wavelength of radiation after the emergence thereof from their respective samples into substantially collinear wavelengths of radiation by utilizing the difference in polarization thereof, polarizing the reunited first wavelength of radiation and the second wavelength of radiation to enable the interference thereof, detecting the interference and generating an electrical interference signal in response thereto, and measuring the phase of the electrical interference signal relative to the phase difference to the initially generated first wavelength of radiation relative to the second wavelength of radiation.

Benefits and advantages of the present invention include: high resolution ($\lambda/7200$), high stability ($\lambda/5000$), minimal alignment required for components, small size and simplicity, lack of model dependence for the measured results, improvement of resolution with sample path length more rapidly than the increase in vibrational and thermal noise as a result thereof over a sizable range, and for the thermooptic spectrophotometer, ease of adjusting the heating intensities to be equal in both probe volumes, and minimal alignment difficulties.

BRIEF DESCRIPTION OF THE DRAWINGS

The accompanying drawings, which are incorporated in and form a part of the specification, illustrate several embodiments of the present invention and, together with the description, serve to explain the principles of the invention. In the drawings.

DETAILED DESCRIPTION OF THE PREFERRED EMBODIMENTS OF THE INVENTION

Briefly, the present apparatus includes a two-frequency, Zeeman-effect laser and doubly refracting crystals in the construction of an accurate interferometer. Unlike other interferometric devices, the present invention exhibits excellent phase stability owing to the use of single piece means for producing parallel interferometer arms. Because of these means, the subject interferometer is relatively insensitive to thermal and mechanical instabilities. Interferometers respond to differences in optical path length between their two arms. Unlike most interferometric techniques, which require the measurement of the location of interference fringes in a brightly illuminated background, the present invention permits the determination of the optical path length difference by measuring the phase of an electronic sine wave. The present apparatus is demonstrated as a differential thermooptic spectrometer which is but one of many applications therefor.

Changes of $\lambda/7200$ in the relative optical path lengths of two samples can be detected with the present interferometer. This resolution is at least a factor of five better than can routinely be achieved using conventional interferometric techniques. The commercially available Optralite two-frequency Zeeman-effect laser generates a 1 mW, HeNe output beam comprising two, collinear laser lines having orthogonal polorizations. The two lines, each near 632.8 nm, differ by 250 kHz out of 474,000 GHz. The 250 kHz frequency is stable to 0.1 ppm. When the two collinear laser lines from the two-frequency laser pass through a properly oriented polarizer, they can interfere. A 250 kHz beat frequency can be observed. The phase of this sine wave equals the optical phase difference between the two laser lines. It would be apparent to one having skill in the art of interferometry that beat frequencies between 0.1 kHz and 500 MHz (differences in wavelength between $1 \times 10^{-13}$ and $7 \times 10^{-4}$ nm) are readily detected. Therefore, as other laser systems which generate two wavelengths of collinear radiation having orthogonal polarizations and a wavelength difference between the bounds cited hereinabove become available, they can be utilized as light sources for interferometric investigations according to the teachings of the present invention.

Figure 1:
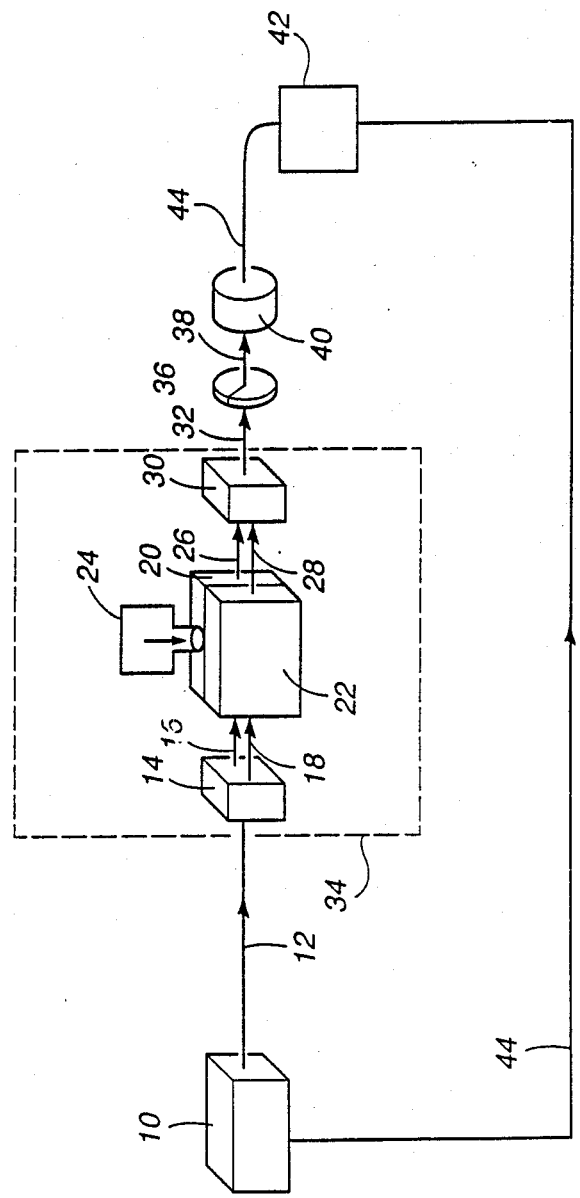
FIG. 1 is a schematic representation of the basic interferometer of the present invention.

Reference will now be made in detail to the present preferred embodiments of the invention, examples of which are illustrated in the accompanying drawings. Turning now to FIG. 1 hereof, therein it is shown a schematic representation of the basic interferometer of the present invention. Two-frequency, Zeeman-effect Laser 10 generates two collinear wavelengths of electromagnetic radiation having orthogonal polarizations 12. The two, close-in-frequency radiations are directed into calcite beam displacer 14 wherein the two wavelengths of radiation are separated into two substantially parallel beams, a first wavelength of radiation, 16 and a second wavelength of radiation 18. Beam 16 is directed into a sample to be analyzed 20, while beam 18 is directed into a reference sample 22. Means for flowing the sample under investigation 24 may be provided if individual particles derived from a flow cytometer or continuously variable samples are to be investigated. Generally, the reference sample will be a static sample. The emerging first wavelength of radiation 26, and the emerging second wavelength of radiation 28 are directed into a second calcite beam displacer 30 which combines the two beams into a substantially collinear pair of wavelengths 32. It should be mentioned that other doubly refracting polarization responsive beam separation and reuniting materials may be employed. For example, magnesium fluoride crystals can be used; however, the beam displacement is much smaller so that large crystals would be required. Temperature control means 34 surrounding the calcite crystals and the samples is provided for controlling the temperature between the crystals to improve interferometer stability when measurements are contemplated which are very lengthy. Focusing optics may be provided to focus beams 16 and 18 into a small volume if the sample under investigation is small. Beam 32 comprising the emerging collinear first and second wavelengths is directed into polarizer 36 which enables the two wavelengths of radiation to interfere with one another. Emerging beam of radiation 38 is detected by photodetector 40. A beat frequency which is equal to the difference in frequency of the two wavelengths of radiation generated by two-frequency, Zeeman-effect Laser 10 is impressed on photodetector 40. The electrical signal generated thereby is directed to phase detector 42. The phase difference between the phase of the detected beat frequency and that of the generated collinear beam 12, as represented electrically by signal 44 from Zeeman-effect Laser 10, is related to the difference in optical path length of the first wavelength of radiation 16 and the second wavelength of radiation 18 through the sample under investigation 20 and the reference sample 22.

Figure 2:
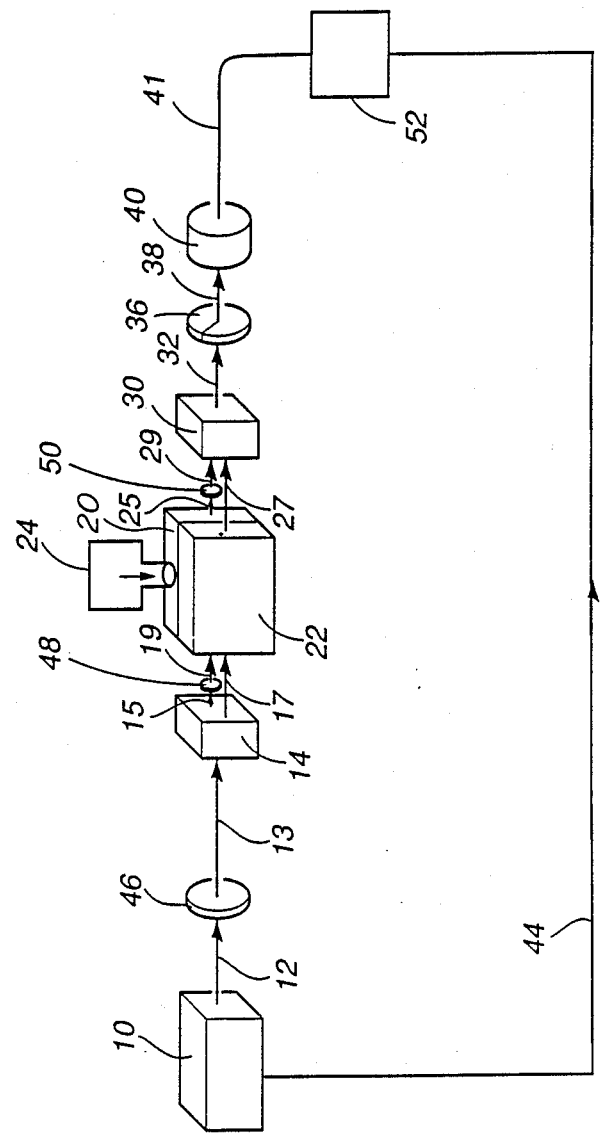
FIG. 2 is a schematic representation of a second embodiment of the interferometer apparatus of the present invention. It is similar to that shown in FIG. 1 hereof except for the modifications which permit the measurement of transient effects such that would occur if a fast moving particle were to intercept the first wavelength of radiation within the sample under investigation.

FIG. 2 is a schematic representation of another embodiment of the interferometer apparatus of the present invention. It is similar to that shown in FIG. 1 hereof. However, it is modified to permit the measurement of transient effects such that would occur if a fast moving particle were to intercept the first wavelength of radiation within the sample under investigation. Beam expander and collimator 46 is inserted into beam 12 producing thereby expanded and collimated beam 13 which is directed into beam separator 14. Emerging beam 15 is then focused by focusing means 48, the emerging second wavelength of radiation 17 not being further altered. The resulting light beam 19 is directed into sample container 20 into which a stream of particles or a sample having changing density, composition, temperature, or some combination thereof is flowed by flowing means 24. Emerging beam 25 is then recollimated using recollimating means 50 to produce light beam 29. The beam 27 emerging from reference sample container 22 is not further altered. Light beams 27 and 29 are reunited in beam combining means 30, the remainder of the apparatus being identical to that of FIG. 1 hereof except for phase detector 52. Here the phase is recorded by a waveform recorder, a pulse-mode lock-in amplifier or a fast phase-to-voltage converter. It is to be mentioned that the particles under investigation derived from flowing means 24 must be directed such that they intersect light beam 19.

Figure 3:
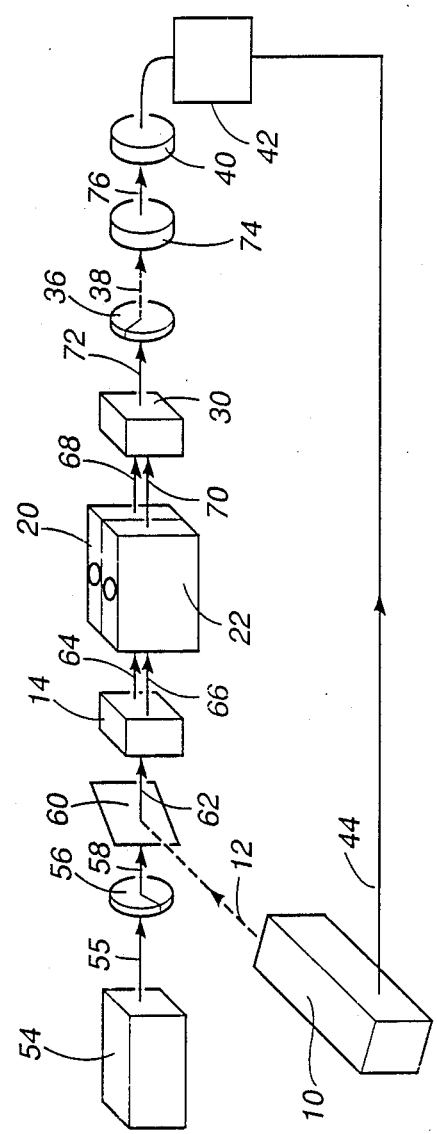
FIG. 3 shows a schematic representation of the apparatus of the present invention utilized as a differential thermooptic spectrophotometer.

FIG. 3 shows a schematic representation of the apparatus of the present invention utilized as a differential thermooptic spectrometer. Heating laser 54 generates electromagnetic energy 55 which is directed into polarizer 56. It is preferred that heating laser 54 have the capability of providing radiation having significantly greater than 1 mW of power and have the capability of being tuned so that absorption of the output thereof can be studied as a function of wavelength. It would be apparent to one having skill in the art of spectroscopy that an incoherent light source could be used in place of heating laser 54 if such a source is well collimated. Heating laser beam 55 is polarized at −45 degrees to the vertical by polarizer 56. Emerging beam 58 is split by calcite beam displacer 14 into two spatially parallel beams. One beam has vertical polarization, while the other is horizontally polarized. The intensities of these two beams can be made substantially equal in the samples' probe volumes by slightly adjusting the angle of polarization provided by polarizer 56 about −45 degrees. The ease and precision with which this can be achieved is a major advantage of the present invention over other differential absorption methods. Highly absorbent samples may be used to improve the accuracy of this adjustment. The collinear laser radiations 12 from two-frequency, Zeeman-effect laser 10 are reflected using beam splitter 60 and combined with polarized heating laser radiation 58 to form beam 62. Since the two Zeeman Effect laser wavelengths 12 have orthogonal linear polarizations, they can be readily separated using calcite beam displacer 14. The laser lines 64, 66 emerging from beam displacer 14 are substantially parallel interferometer probe beams, one having vertical polarization and the other parallel polarization. The intensities of probe beams 64, 66 need not be exactly equal because of their relatively low power (less than 0.5 mW). It is necessary that the heating laser radiation and the probe beams be substantially collinear inside of the sample under investigation 20 and inside the reference sample 22. Each parallel beam 64, 68 and 66, 70 serves as one arm of the spectrometer. Typically, the reference sample 22 is a pure solvent. The sample to be investigated spectrophotometrically 20 would then contain the same solvent plus a small quantity of solute to be measured for absorptivity. It would be apparent to one having ordinary skill in the art of spectrophotometry that heating laser 54 would be unnecessary if the two-frequency Zeeman-effect laser radiation is absorbed by the solute to be investigated and the power thereof is sufficient to induce significant heating in the sample under investigation. After traversing the samples, the two laser wavelengths 68, 70 are again made collinear 72 by calcite beam displacer 30, which is substantially identical to calcite beam displacer 14. Thus, the two matched, doubly refracting calcite crystals 14, 30 serve to first separate and then reunite, respectively, the two arms of the interferometer. It would be apparent to one having ordinary skill in the art of spectrophotometry that each of crystals 14 and 30 could be replaced by two Ronchon prism polarizers to produce or reunite the two parallel beams. However, such a configuration would not be as stable as the single rigid means according to the teachings of the present invention. Beam 72 is then directed into polarizer 36 having its transmission axis at +45 degrees to the vertical before reaching photodiode 40. Polarizer 36 permits the two wavelengths of radiation to interfere on photodiode 40 so that the beat frequency can be detected. Polarizer 36 also serves to block a substantial portion of the heating laser radiation. The exact angle of the transmission axis for this polarizer is not critical, so that the angle of polarizer 36 can be adjusted to minimize the amount of heating beam reaching the photodiode. Complete elimination of the heating beam from the photodetector is ordinarily unnecessary since it does not contain ac components in the region of the beat frequency. In the rare circumstance where a reduction of heating beam reaching the detector is required below that permitted by the polarizer, a wavelength separation device such as interference filter or diffraction grating 74 may be employed. As the sample under investigation absorbs more of the heating beam radiation than the reference sample, the difference in the optical path lengths of the two samples will vary with time. This will result in a change of phase of the beat frequency sine wave. The phase can readily be measured using a phase meter or a lock-in amplifier 42. A sine wave 44 reflecting the frequency difference between the first wavelength of radiation and the second wavelength of radiation is generated by the two-frequency Zeeman-effect laser and is used as a phase reference.

Figure 4:
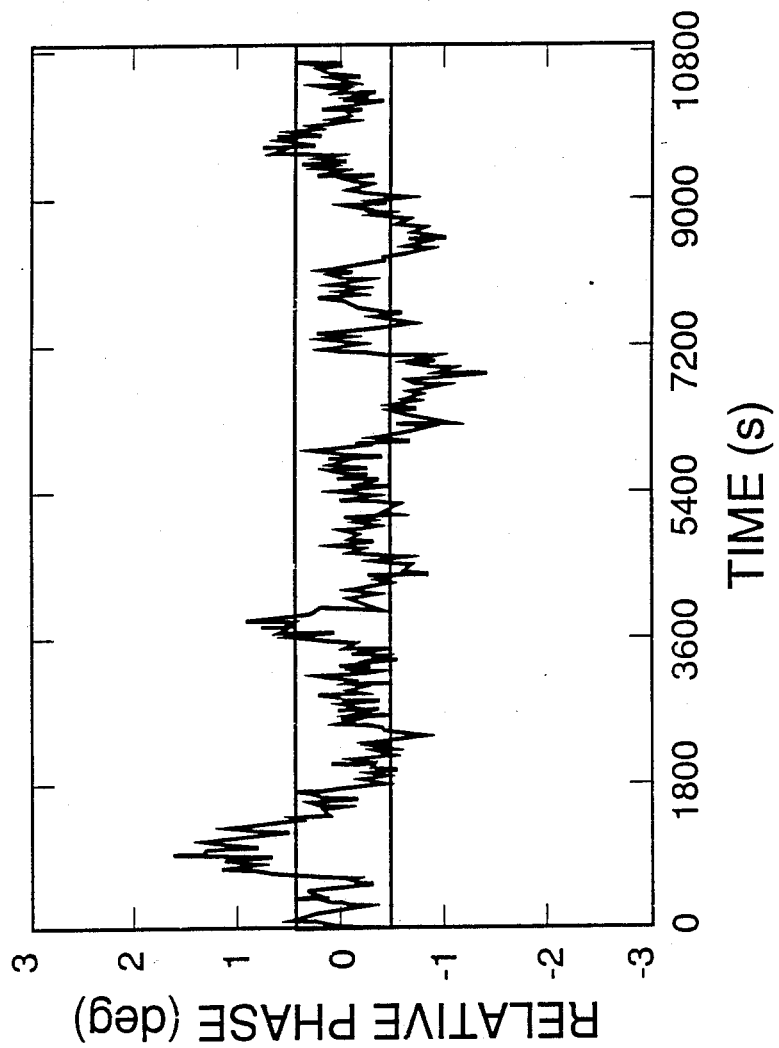
FIG. 4 is an illustration of the bulk interferometer stability of the apparatus of the present invention with ±8 mK temperature control.

The interferometer of the present invention is relatively insensitive to vibrations and thermal fluctuations as will be illustrated in FIG. 4 hereof. The two laser wavelengths generated by the two-frequency laser are collinear through most of the present apparatus. They are parallel and slightly displaced only between the two doubly refractive crystals. As a result, movements or thermal fluctuations in the interferometer tend to affect both Zeeman laser wavelengths approximately equally. FIG. 4 is an illustration of the bulk interferometer stability with ±8 mK temperature control. The solid horizontal lines represent $\pm \lambda/720 = \pm 0.5$ degrees in phase $= 9 \times 10^{-8}$ in relative refractive index. The phase resolution is ten times better than the stability. However, without temperature stabilization, the stability is ±0.5 degrees in phase shift ($\pm \lambda/720$) over a 1 min. period, which is more than sufficient for thermooptic absorption measurements.

Figure 5:
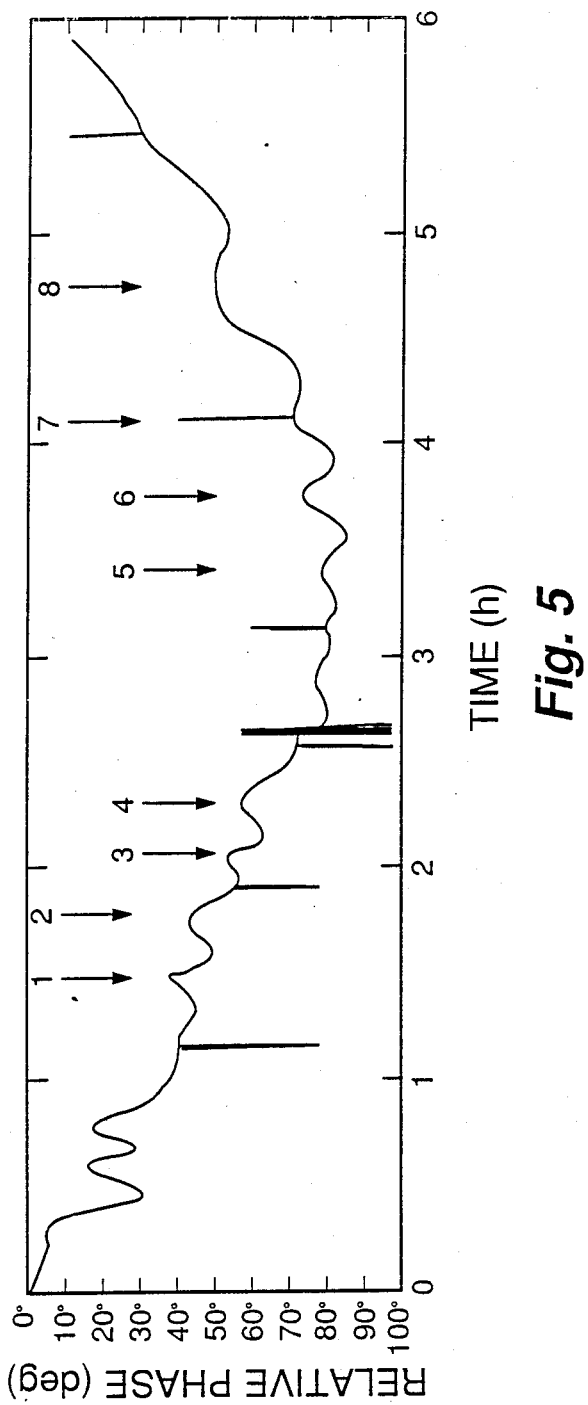
FIG. 5 shows the real time detection of DNA bands (relative phase versus time) in a gel electrophoresis experiment using the apparatus of the present invention.

FIG. 5 shows the real time detection of DNA bands (relative phase versus time) in a gel electrophoresis experiment using the apparatus of the present invention. A stained, untagged sample of DNA having approximately 50 ng entered the unfocused beam of the two-frequency, Zeeman-effect laser during electrophoresis at position 20 in FIG. 1. In the first hour of electrophoresis, the curve shows the passage of the salt front and dye through one of the beams. At later times, the numbers above the curve show at which point the DNA bands pass through one of the beams. The sharp features are artifacts representing momentary lockage of the light beam during the experiment. Focusing the beam would give greater sensitivity, but would simultaneously increase the instability of the system. The slow phase drift is due to the lack of temperature control of the interferometer. It should be pointed out that the DNA bands can be detected as unstained bands. Moreover, the described application to electrophoresis would be essentially identical to the use of the present invention for liquid or gas chromatography applications.

Figure 6:
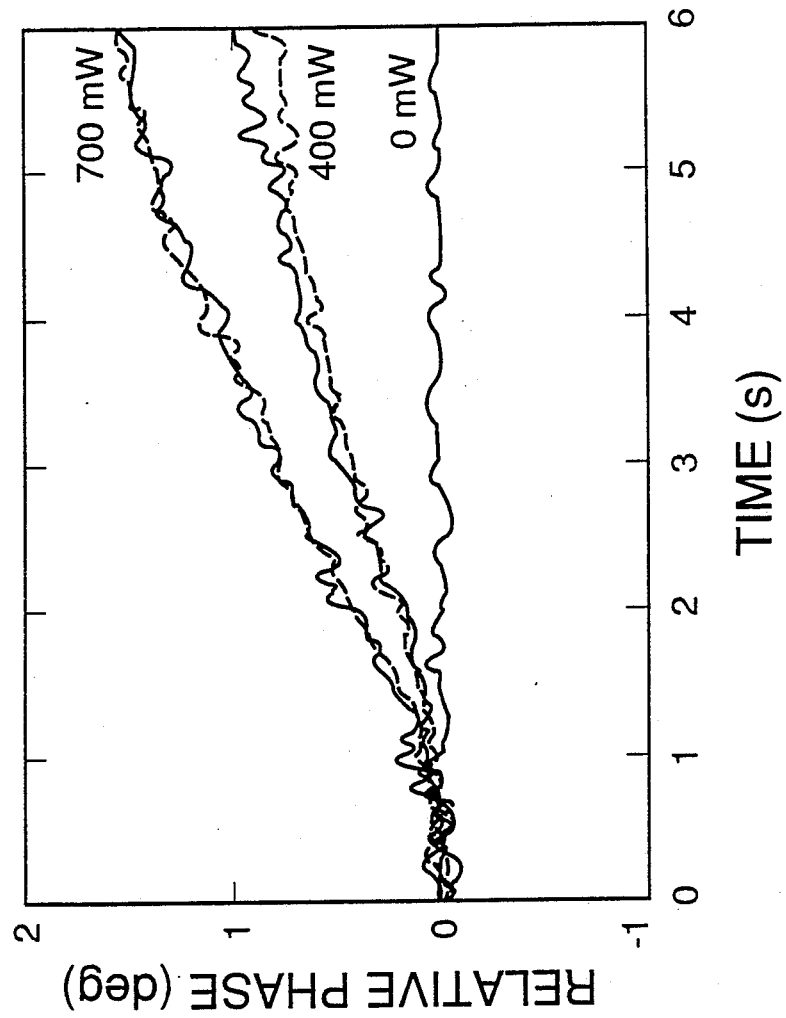
FIG. 6 shows data (relative phase versus time) obtained using the present interferometer apparatus as a thermooptic spectrophotometer described in FIG. 3 hereof.

FIG. 6 shows data (relative phase versus time) obtained using the present interferometer apparatus as a thermooptic spectrophotometer. The three solid curves represent three heating laser power levels as indicated by the numbers approximating the power level on the right hand side of the curves. The sample under investigation was $8 \times 10^{-12}$ moles/liter of Sudan IV, a biological dye, in a 1 cm path length cell. This corresponds to an optical density of $2 \times 10^{-7}$ ($\alpha = 5 \times 10^{-7}$ cm$^{-1}$).

The foregoing description of the preferred embodiments of the invention has been presented for purposes of illustration and description. It is not intended to be exhaustive or to limit the invention to the precise form disclosed, and obviously many modifications and variations are possible in light of the above teaching. For example, the thermooptic spectrophotometer of the present invention could be used to measure the linear dichroism and circular dichroism of samples. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What I claim is:

1. An apparatus for measuring the optical phase difference resulting from a difference in index of refraction between a sample under investigation and a reference sample, said apparatus comprising in combination:
   a. a light source for providing a first wavelength of electromagnetic radiation and a second wavelength of electromagnetic radiation, the first radiation and the second radiation being substantially collinear, having substantially orthogonal polarization and an initial relative phase, and differing in wavelength by between $1 \times 10^{-13}$ nm and $7 \times 10^{-4}$ nm;
   b. radiation separation means responsive to polarization for receiving the first wavelength of radiation and the second wavelength of radiation and for spatially separating the first wavelength of radiation and the second wavelength of radiation into substantially parallel wavelengths of radiation, the first wavelength of radiation passing through the sample under investigation and the second wavelength of radiation passing through the reference sample;
   c. radiation combining means similar to said radiation separation means responsive to polarization for receiving the first wavelength of radiation after the emergence thereof from the sample under investigation, and for receiving the second wavelength of radiation after the emergence thereof from the reference sample. and for spatially reuniting the first wavelength of radiation and the second wavelength of radiation into substantially collinear wavelengths of radiation;
   d. first polarization means having a chosen angle of polarization for receiving the reunited first wavelength of radiation and second wavelength of radiation and for enabling the interference thereof;
   e. electromagnetic radiation detection means for receiving the interfering first wavelength of radiation and second wavelength of radiation and for generating an electrical interference signal in response thereto; and
   f. phase detection means for receiving the electrical interference signal generated by said electromagnetic radiation detection means and for measuring the phase thereof relative to the initial relative phase of the first wavelength of radiation and the second wavelength of radiation.

2. The apparatus as described in claim 1, further comprising first containment means for containing the sample under investigation and second containment means for containing the reference sample.

3. The apparatus as described in claim 2, further comprising means for flowing the sample under investigation through said first containment means.

4. The apparatus as described in claim 2, further comprising means for flowing particles to be investigated through said first containment means.

5. The apparatus as described in claim 4, further comprising means for focusing the first wavelength of radiation into said first containment means into which particles are being flowed such that the flowing particles intercept the focused first wavelength of radiation approximately in the region of the focus thereof.

6. The apparatus as described in claim 5, further comprising recollimating means for recollimating the focused first wavelength of radiation subsequent to the emergence thereof from said first containment means and before the entrance thereof into said radiation combining means.

7. The apparatus as described in claim 6, further comprising beam expanding means for expanding and collimating the first wavelength of radiation and the second wavelength of radiation subsequent to the emergence thereof from said light source.

8. The apparatus as described in claim 2, further comprising temperature control means surrounding said first containment means, said second containment means, said radiation separation means, and said radiation combining means for maintaining the temperature thereof substantially constant.

9. The apparatus as described in claim 1, wherein said radiation separation means and said radiation combining means include matched doubly refractive optical material.

10. The apparatus as described in claim 9, wherein said radiation separation means and said radiation combining means include matched calcite beam displacers.

11. The apparatus as described in claim 9, wherein said radiation separation means and said radiation combining means include matched magnesium fluoride beam displacers.

12. The apparatus as described in claim 1, wherein said light source for providing the first wavelength of electromagnetic radiation and the second wavelength of electromagnetic radiation includes a two-frequency, Zeeman-effect Laser.

13. A method for measuring the optical phase difference resulting from a difference in index of refraction between a sample under investigation and a reference sample, said method comprising the steps of:
 a. generating of first wavelength of electromagnetic radiation and a second wavelength of electromagnetic radiation, the first radiation and the second radiation being substantially collinear, having substantially orthogonal polarization and an initial relative phase, and differing in wavelength by between $1 \times 10^{-13}$ nm and $7 \times 10^{-4}$ nm;
 b. spatially separating the first wavelength of radiation and the second wavelength of radiation by utilizing the difference in polarization thereof into substantially parallel wavelengths of radiation;
 c. directing the first wavelength of radiation into the sample under investigation;
 d. directing the second wavelength into the reference sample;
 e. spatially combining the first wavelength of radiation after the emergence thereof from the sample under investigation and the second wavelength of radiation after the emergence thereof from the reference sample into substantially collinear wavelengths of radiation by utilizing the difference in polarization thereof;
 f. maintaining the temperature substantially constant for said steps of spatially separating the first wavelength of radiation and the second wavelength of radiation, spatially combining first wavelength of radiation and the second wavelength of radiation, directing the first wavelength of radiation into the sample under investigation, and directing the second wavelength of radiation into the reference sample;
 g. polarizing the reunited first wavelength of radiation and the second wavelength of radiation at a chosen polarization angle to enable the interference thereof;
 h. detecting the interference of the first wavelength of radiation and the second wavelength of radiation and generating an electrical interference signal in response thereto; and
 i. measuring the phase of the electrical interference signal relative to the phase difference of the initially generated first wavelength of radiation relative to the second wavelength of radiation.

14. The method as described in claim 13, further comprising the steps of flowing the sample under investigation such that it intersects the path of the first wavelength of radiation after said step of spatially separating the first wavelength of radiation and the second wavelength of radiation.

15. The method as described in claim 13, further comprising the step of flowing particles under investigation such that the particles intersect the path of the first wavelength of radiation after said step of spatially separating the first wavelength of radiation and the second wavelength of radiation.

16. An apparatus for measuring small differences in optical absorption between a sample under investigation and a reference sample utilizing the thermooptic effect, said apparatus comprising in combination:
 a. a light source for providing a first wavelength of electromagnetic radiation and a second wavelength of electromagnetic radiation, the first radiation and the second radiation being substantially collinear, having substantially orthogonal polarization and a initial relative phase, and differing in wavelength by between $1 \times 10^{-13}$ nm and $7 \times 10^{-4}$ nm;
 b. radiation separation means responsive to polarization for receiving the first wavelength of radiation and the second wavelength of radiation and for spatially separating the first wavelength of radiation and the second wavelength of radiation into substantially parallel wavelengths of radiation, the first wavelength of radiation intersecting the sample under investigation and the second wavelength of radiation intersecting the reference sample;
 c. radiation combining means similar to said radiation separation means responsive to polarization for receiving the first wavelength of radiation after the emergence thereof from the sample under investigation, and for receiving the second wavelength of radiation after the emergence thereof from the reference sample, and for spatially reuniting the first wavelength of radiation and the second wavelength of radiation into substantially collinear wavelengths of radiation;
 d. first polarization means having a chosen angle of polarization for receiving the reunited first wavelength of radiation and the second wavelength of radiation and for enabling the interference thereof;
 e. electromagnetic radiation detection means for receiving the interfering first wavelength of radiation and the second wavelength of radiation and for generating an electrical interference signal in response thereto; and
 f. phase detection means for receiving the electrical interference signal generated by said electromagnetic radiation detection means and for measuring the phase thereof relative to the initial relative phase of the first wavelength of radiation and the second wavelength of radiation.

17. The apparatus as described in claim 16, further comprising electromagnetic radiation heating means for generating high power electromagnetic radiation, second polarization means having an adjustable polarization angle substantially orthogonal to the polarization angle of said first polarization means for receiving the high power electromagnetic radiation and transmitting the high power electromagnetic radiation with a chosen polarization angle, and beam splitting means for receiving the high power electromagnetic radiation and the first wavelength of radiation and the second wavelength of radiation, for combining the high power electromagnetic radiation and the first wavelength of radiation and the second wavelength of radiation into a collinear beam of electromagnetic radiation, and for directing the collinear beam of electromagnetic radiation into said radiation separation means, wherein the intensity of the high power electromagnetic radiation directed into the sample under investigation and that directed into the reference sample can be made substantially equal, and wherein the high power electromagnetic radiation directed into the sample under investigation is substantially collinear with the first wavelength of radiation directed thereinto and the high power electromagnetic radiation directed into the reference sample is substantially collinear with the second wavelength of radiation directed thereinto.

18. The apparatus as described in claim 17, further comprising first containment means for enclosing the sample under investigation and second containment means for enclosing the reference sample.

19. The apparatus as described in claim 17, wherein said light source for providing the first wavelength of electromagnetic radiation and the second wavelength of electromagnetic radiation includes a two-frequency, Zeeman-effect Laser.

20. The apparatus as described in claim 17, wherein said electromagnetic heating means includes a laser.

21. The apparatus as described in claim 20, further comprising wavelength separating means for substantially reducing the high power electromagnetic radiation reaching said electromagnetic radiation detection means, said wavelength separating means being disposed in such a manner as to intercept any high power electromagnetic radiation passing through said first polarization means.

22. The apparatus as described in claim 21, wherein said wavelength separating means includes an interference filter.

23. The apparatus as described in claim 16, wherein said radiation separation means and said radiation combining means include matched doubly refractive materials.

24. The apparatus as described in claim 23, wherein said radiation separation means and said radiation combining means include matched calcite beam displacers.

25. The apparatus as described in claim 23, wherein said radiation separation means and said radiation combining means include matched magnesium fluoride beam displacers.

* * * * *